United States Patent [19]

Wanner et al.

[11] Patent Number: 5,413,920
[45] Date of Patent: May 9, 1995

[54] METHOD FOR ENHANCED PRODUCTION AND RECOVERY OF PHOSPHATE STARVATION INDUCIBLE GENE PRODUCTS

[75] Inventors: Barry L. Wanner, West Lafayette, Ind.; Ki-Sung Lee, Daejon, Rep. of Korea; William W. Metcalf, West Lafayette, Ind.

[73] Assignee: Purdue Research Foundation, West Lafayette, Ind.

[21] Appl. No.: 192,776

[22] Filed: Feb. 7, 1994

Related U.S. Application Data

[63] Continuation of Ser. No. 865,089, Apr. 8, 1992, abandoned.

[51] Int. Cl.$^6$ ............... C12P 21/00; C12P 1/04; C12N 9/88
[52] U.S. Cl. .................. 435/71.2; 435/69.1; 435/71.1; 435/196; 435/244; 435/822; 435/849; 435/232
[58] Field of Search .............. 435/71.1, 71.2, 196, 435/244, 822, 849, 232, 69.1

[56] References Cited

PUBLICATIONS

Makino et al. Jour Bacter Apr. 1991 pp. 2665–2672 vol. 173 No. 8.

Chen et al. Jour Biol Chem. Mar. 15, 1990 vol. 265 No. 8 pp. 4461–4471.

Gray et al., Periplasmic Production of Correctly Processed Human Growth Hormone in *Escherichia coli*: Natural and Bacterial Signal Sequences are Interchangeable, *Gene*, vol. 39, pp. 247–254 (1985).

Wanner, Novel Regulator Mutants of the Phosphate Regulon in *Escherichia coli* K–12 *J. Mol. Biol.* vol. 191, pp. 39–58 (1986).

Wanner et al., Phosphate-controlled Gene Expression in *Escherichia coli* Using MudI-directed lacZ Fusions, J. Mol. Biol. vol. 158, pp. 347–363 (1983).

Metcalf et al., Involvement of the *Escherichia coli phn* (psiD) Gene Cluster in Assimilation of Phosphorus in the Form of Phosphonates, Phosphate, Pi esters, and Pi, *J. Bacteriol.* vol. 173, pp. 587–600 (1991).

Murata, et al., A Microbial Carbon–Phosphorous Bond Cleavage Enzyme Requires Two Protein Components for Activity, *J. Bacteriol* vol. 171, pp. 4504–4506 (1989).

Wackett et al., Involvement of the Phosphate Regulon and the psiD Locus in the Carbon–Phosphorus Lyase Activity of *Escherichia coli* K–12, *J. Bacteriol.* vol. 169, pp. 1753–1756.

Wanner et al., Mapping and Molecular Cloning of phn (psiD) Locus for Phosphonate Utilization in *Escherichia coli, J. Bacteriol.* vol. 172, pp. 1186–1196 (1990).

*Primary Examiner*—Herbert J. Lilling
*Attorney, Agent, or Firm*—Woodard, Emhardt, Naughton, Moriarty & McNett

[57] ABSTRACT

A method for enhanced production and recovery of phosphate starvation inducible (PSI) gene products. A bacterium having C-P lyase activity is cultured using phosphonate or phosphite (or their mixtures) as the predominant phosphorus source for growth so as to enhance PSI gene product accumulation. PSI gene product is then recovered.

19 Claims, 4 Drawing Sheets

METHOD FOR ENHANCED PRODUCTION AND RECOVERY OF PHOSPHATE STARVATION INDUCIBLE GENE PRODUCTS

This application is a continuation of application Ser. No. 07/865,089, filed Apr. 8, 1992, now abandoned.

BACKGROUND

The present invention relates generally to methods for producing gene products. More particularly, it relates to a method for enhanced production and recovery of phosphate starvation inducible gene products.

By way of further background, bacteria use phosphate, phosphate esters, or phosphonates as phosphorus sources for growth. However, phosphate is the preferred phosphorus source. When in excess, phosphate leads to repression of genes for use of alternative phosphorus sources, phosphate esters or phosphonates. Genes for use of alternative phosphorus sources are turned on several hundred fold during phosphate limitation. Such genes are phosphate starvation inducible and are thus known as PSI genes. As to utilization of phosphonates, it is known that two pathways for their breakdown exist. These include the carbon-phosphorus ("C-P") lyase pathway and the phosphonatase pathway. As is known, these pathways are distinguishable by substrate specificity and product formation.

Phosphate limitation, which by nature limits growth yield, is a conventional means for the expression of both natural and synthetic PSI genes at a high rate to provide gene products used in assays (e.g. immunoassays), therapies (e.g. growth hormones) and other applications. However, phosphate starvation limits growth yield, and thus the final (total) amount of the PSI gene product is limited, as well.

In light of this background there continues a need for an economical method for enhancing the production and recovery of PSI gene products which does not suffer from limited growth yield. The present invention addresses this need.

SUMMARY OF THE INVENTION

One preferred embodiment of the invention provides a method for enhanced production and recovery of phosphate starvation inducible gene product. This method includes the step of culturing a bacterium having C-P lyase activity on phosphonate or phosphite or a mixture thereof as the predominant phosphorus source for growth to result in enhanced accumulation of gene product. The gene product is then recovered.

One object of the invention is to provide an improved method for production and recovery of PSI gene products.

Another object of the invention is to provide a method of production and recovery of PSI gene product which does not suffer from limited growth yield as do conventional methods using phosphate limiting conditions.

Another object of the invention is to provide PSI gene product synthesis capitalizing on the discovery that enhanced PSI gene product production is obtained throughout the logarithmic growth phase when phosphonate or phosphite is used as the predominant phosphorus source during microbial growth.

Another object of this invention is to provide a method for enhanced production and recovery of PSI gene products which can be directly applied to many bacterial expression systems now in use for expression of PSI genes, for synthesis of their gene products.

Still another object of the invention is to provide a method which can be applied over a wide range of culture conditions to achieve enhanced production efficiency of PSI gene products.

Additional objects and advantages of the invention will be apparent from the following description.

Figure 1A:
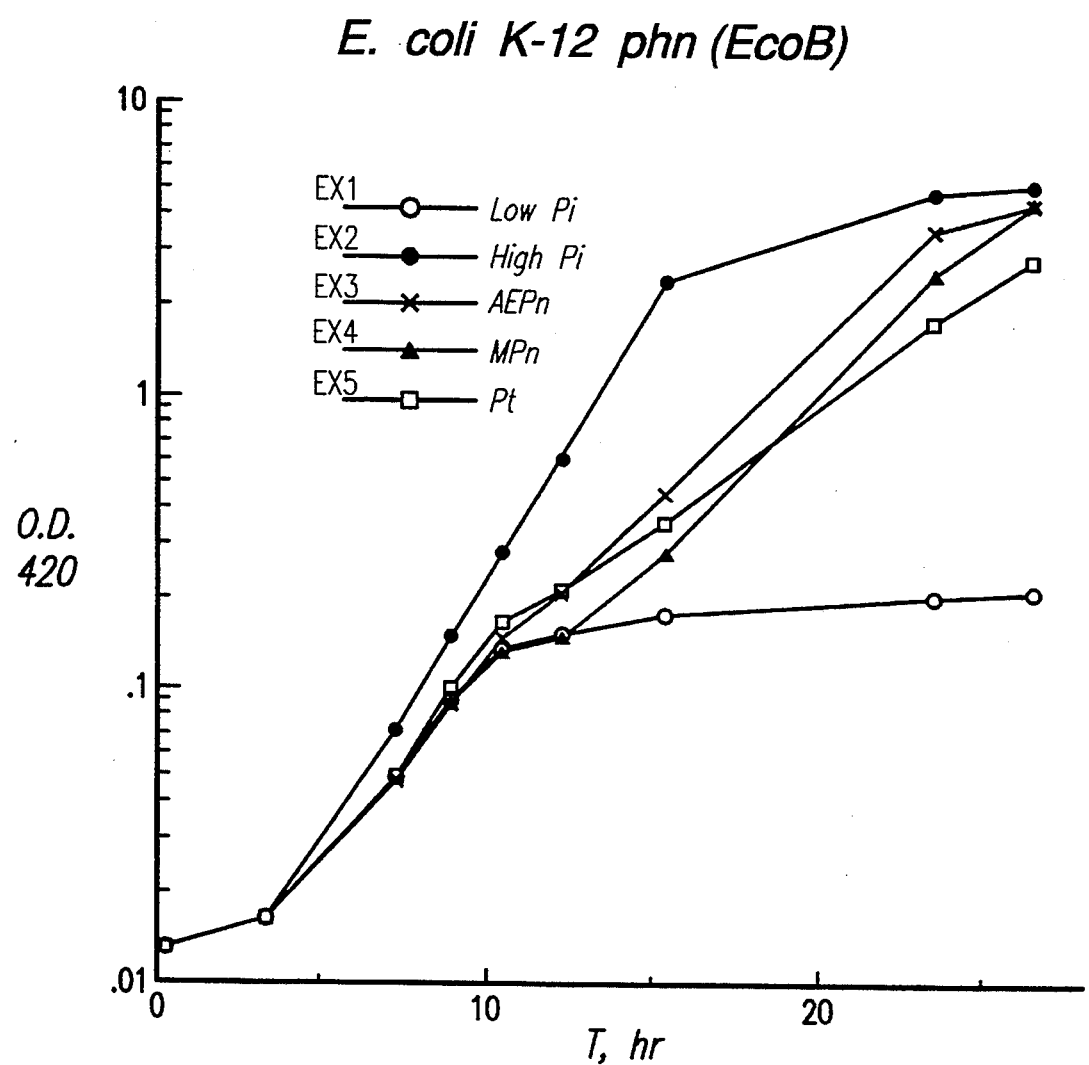
FIG. 1 includes parts 1A and 1B. Part 1A is a plot of O.D. at 420 over time of *E. coli* cultures grown on various phosphorus sources. Part 1B provides a differential plot of Bap synthesis in these same *E. coli* cultures.

Part 2 includes parts 2A and 2B. 2A is a plot of O.D. at 420 over time of *Ent. aerogenes* cultures grown on various phosphorus sources. Part 2B provides a differential plot of Bap synthesis in these same *Ent. aerogenes* cultures.

DESCRIPTION OF THE PREFERRED EMBODIMENT

To promote an understanding of the principles of the invention, reference will now be made to a certain embodiment and specific language will be used to describe the same. It will nevertheless be understood that no limitation of the scope of the invention is thereby intended, such alterations and further modifications and applications of the principles of the invention being contemplated as would normally occur to one skilled in the art to which the invention relates.

As indicated, one preferred embodiment of the invention relates to a method for enhanced production and recovery of phosphate starvation inducible gene product. In this regard, as used herein the term "enhanced" means that the amount of PSI gene product accumulated in the culture medium is increased due to growth of the cells on phosphonate, phosphite or their mixtures. In preferred methods, these enhanced amounts are resultant of increased production of PSI gene product throughout the logarithmic growth phase of the culture. Similarly, the term "predominant phosphorus source for growth" as used herein in connection with phosphonate, phosphite or their mixtures means that more growth is due to these sources than is to inorganic phosphate or other phosphorus sources. It is preferred that the phosphonate, phosphite or their mixture be present in molar excess to any inorganic phosphorus present (the phosphonate, phosphite or their mixture can be used as the sole phosphorus source if desired). For example, such molar excesses of at least 10-fold and even 100-fold or more can also be used to advantage. It is also preferred that the phosphonate, phosphite or their mixtures be present in sufficient amount so as not to limit the final growth yield.

Phosphonates are generally preferred substrates, and include a wide range of phosphonates known and readily available either commercially or by conventional preparations. Particularly preferred phosphonates from work to date include substituted and unsubstituted alkylphosphonates such as methylphosphonate, ethylphosphonate, propylphosphonate, α-aminoethylphosphonate, phosphonoacetate and the like. However, as indicated, these are preferred phosphonates, and other phosphonates which are taken-up, are non-toxic, and which do not form toxic byproduct will be suitable.

The bacterium used in the invention can be any which exhibits C-P lyase activity. These include bacteria in which genes for the C-P lyase pathway are naturally present, in which cryptic C-P lyase genes are activated by mutation, in which genes for the C-P lyase pathway are introduced artificially, for example by gene cloning or gene transfer, and in which these genes may be present in single copy on a chromosome or in multiple copy on plasmids. Additionally, other cells such as eukaryotic cells which exhibit C-P lyase activity will be suitable substitutes for bacteria, although bacteria are preferred.

In this regard, bacteria having C-P lyase activity are known to the art and literature, and commonly include gram-negative bacteria such as *E. coli* and *Enterobacter aerogenes*, for example *E coli* K-12, *E. coli* B, some mutant or hybrid *E. coli*, and *Ent. aerogenes* IFO12010 (from American Type Culture Collection, Rockville, Md, accession number ATCC 15038). For additional information as to exhibition of C-P lyase activity, reference can be made to literature on the subject, including Wackett, L. P., B. L. Wanner, C. P. Venditti, and C. T. Walsh, Involvement of the Phosphate Regulon and the psiD Locus in the Carbon-Phosphorus Lyase Activity of *Escherichia coli* K-12, *J. Bacteriol.* Vol. 169, pp. 1753-1756 (1987); Wanner, B. L., and J. A. Boline, Mapping and Molecular Cloning of the phn (psiD) Locus for Phosphonate Utilization in *Escherichia coli, J. Bacteriol.* Vol. 172, pp. 1186-1196 (1990); Metcalf, W. W. and B. L. Wanner, Involvement of the *Escherichia coli* phn (psiD) Gene Cluster in Assimilation of Phosphorus in the Form of Phosphonates, Phosphate, Pi esters, and Pi, *J. Bacteriol.* Vol 173, pp. 587-600 (1991); and Murata, K., N. Higaki, and A. Kimura, A Microbial Carbon-Phosphorous Bond Cleavage Enzyme Requires Two Protein Components for Activity, *J. Bacteriol* Vol. 171, pp. 4504-4506 (1989).

It has been discovered that bacteria enhancedly produce PSI gene product throughout the logarithmic growth phase when grown on phosphonate broken down by the C-P lyase pathway or phosphite, and that significantly increased amounts of PSI gene product are thereby accumulated and can be recovered, and if desired brought to substantial purity, in a conventional manner. As mentioned above, some bacteria also have a phosphonatase pathway by which phosphonates are broken down. It has further been discovered that PSI genes are expressed only transiently at an enhanced level and then at a lowered level when bacteria are grown with a phosphonate broken down by this phosphonatase pathway. Thus, where the bacterium employed has both C-P lyase and phosphonatase pathways (e.g. *Ent. aerogenes* IFO12010), it is preferred to use a phosphonate broken down by the C-P lyase pathway but not by the phosphonatase pathway. For example, α-aminoethylphosphonate is broken down by both pathways and is thus a non-preferred phosphonate for use with bacteria with both pathways. On the other hand, other phosphonates (e.g. unsubstituted alkylphosphonates) are not broken down by the phosphonatase pathway and are thus preferred substrates for use with bacteria having both pathways.

The PSI gene product can be native or foreign to the bacterium, natural or synthetic, and can include for instance both bacterial and foreign proteins. For example, the gene product may be a natural or mutant bacterial protein such as a bacterial alkaline phosphatase (Bap), or a natural or mutant foreign protein such as a growth hormone, including mammalian growth hormones such as human growth hormone, which can be expressed as phosphate starvation inducible gene products. See, for example, *Gene*, Vol. 39, pp. 247-254 (1985).

Apart from the phosphorus source, the growth medium used in the method of the invention can be conventional, as can other aspects of the fermentation. For instance, synthetic or natural media can be used that contain the usual components such as carbon sources, nitrogen sources, inorganic salts and other nutrients which are assimilated by the bacterium employed. As typical carbon sources there may be mentioned saccharides such as glucose, fructose, sucrose, molasses, starch and starch hydrolyzate, organic acids such as acetic acid, fumaric acid and citric acid, alcohols such as ethanol, methanol, glycerol, etc. Nitrogen sources can include inorganic nitrogen salts (e.g. ammonium chloride and ammonium sulfate), organic nitrogen salts (e.g. ammonium fumarate), amines such as ethylamine, as well as other nitrogen-containing compounds or nitrogeous organic substances (e.g. urea, peptone, yeast or meat extract, corn steep liquor, etc.). As is known, vitamins, amino acids and the like can also be included in the growth medium.

Fermentations are preferably conducted using at least substantially optimum growth conditions for the bacterium employed, and can take up to a day or two or more to complete when conducted in a batchwise fashion. Generally speaking, such fermentations are conducted at temperatures ranging from about 20° to about 40° C. and at pH's ranging from about 5 to about 9 (and more often at approximately neutrality). During such preferred fermentations, high optical densities (O.D.'s) are achieved, for example O.D.'s of 50 or more and even 100 or more (taken at wavelength=420 nm) are achieved. Additionally, the method of the invention can be carried out in both aerobic and anaerobic cultures. Aerobic cultures are preferred, however, since these generally attain higher growth yields.

The accumulated gene product can be recovered by conventional means after the completion of the culturing. For example, the gene product may be released by the bacterium into the surrounding medium, or the cells may be broken (e.g. by sonication, mechanical forces, etc.) to release the gene product. The culture medium can then be further treated by a proper combination of standard techniques such as filtration, centrifugation, treatment of filtrates or supernatants with ion-exchange resin, concentration, etc.

For the purposes of promoting a further understanding of the invention and its features and advantages, the following examples are provided. It will be understood that these examples are illustrative, and not limiting, of the invention.

EXAMPLES 1-10

PSI Gene Product Synthesis With Varying Phosphorous Sources

Synthesis of a PSI gene product (bacterial alkaline phosphatase, "Bap") was carried out by culturing *E. coli* (Examples 1-5) and *Ent. aerogenes* (Examples 6-10) using various phosphorus sources including methylphosphonae (MPn), α-aminoethylphosphonate (AEPn), phosphite (Pt), excess inorganic phosphate (High Pi) and limiting inorganic phosphate (Low Pi). Most media and chemicals were the same as described in Metcalf, W. W., and B. L. Wanner, *J. Bacteriol.* (1991), supra; Wanner, B. L., Novel Regulator Mutants of the Phosphate Regulon in *Escherichia coli* K-12, *J. Mol. Biol.* Vol. 191, pp. 39–58 (1986); and Wanner, B. L., and J. A. Boline, *J. Bacteriol.*, (1990), supra.

Tryptone-yeast extract (TYE) and glucose M63 or glucose morpholinepropane sulfonic acid (MOPS) media were used conventionally as complex and minimal media, respectively. Solid media contained 1.5% Bacto agar (Difco Laboratories, Detroit, Mich.).

Figure 1B:
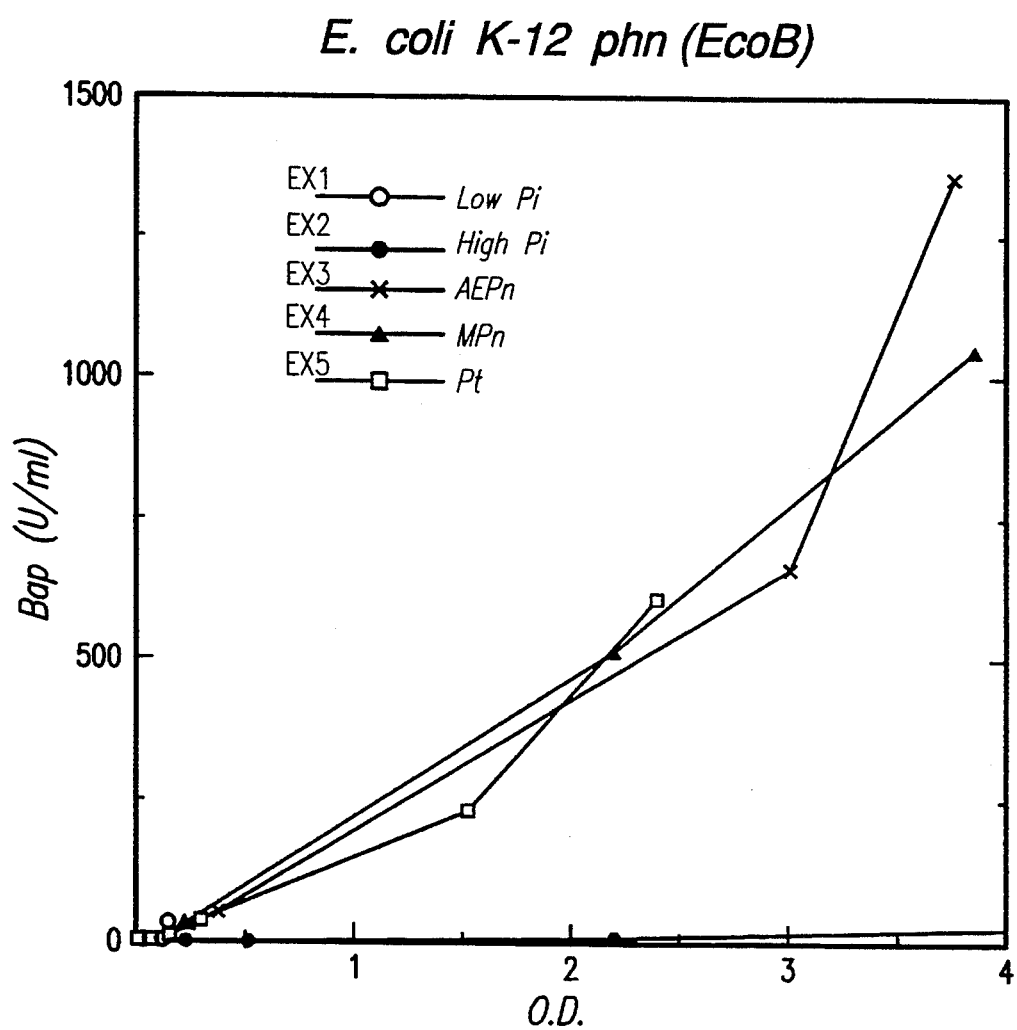
Figure 2A:
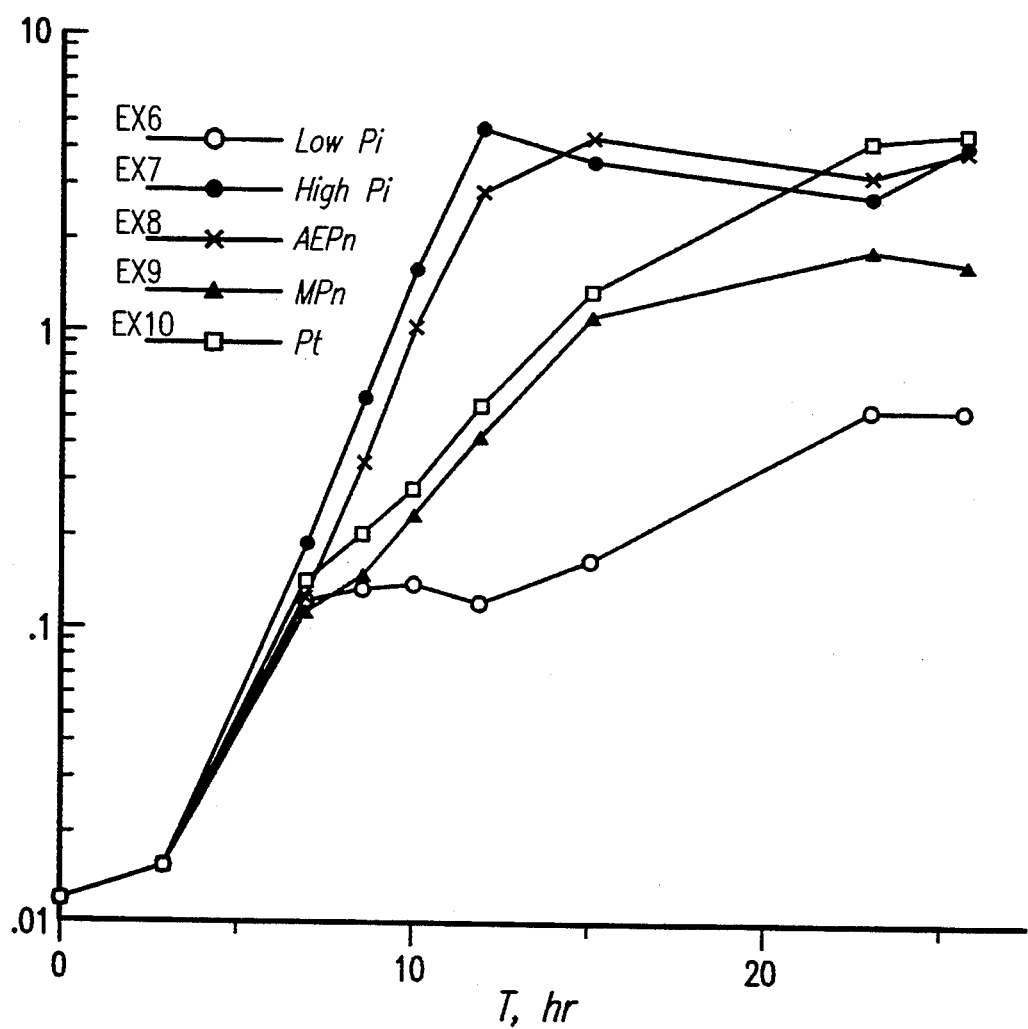
Figure 2B:
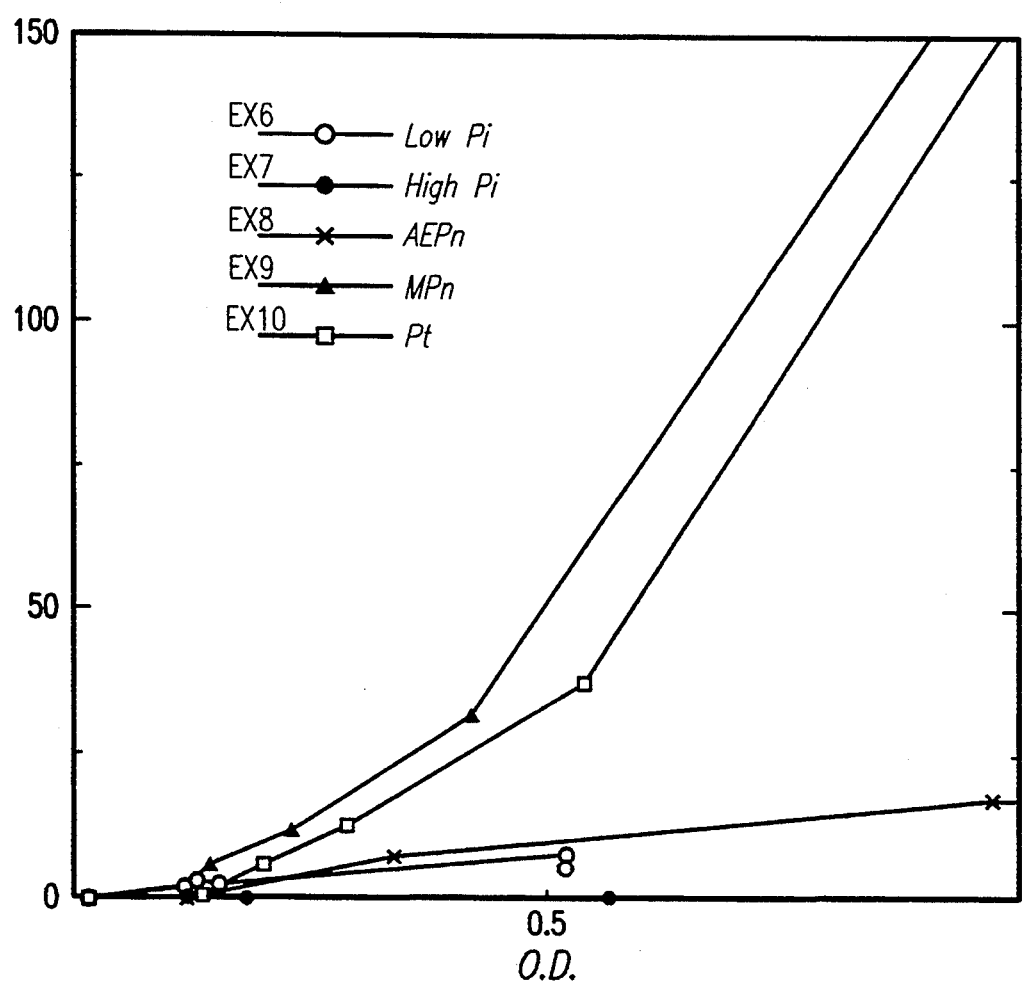

Colonies were pregrown on glucose-MOPS 0.1 mM Pi agar for 24 hours. Cells were suspended in 0.85% saline and inoculated into 25 ml 0.4% glucose-MOPS media with limiting (0.0125 mM) Pi or 0.0125 mM Pi plus 0.5 mM Pi, AEPn, MPn, or Pt. Cultures were aerated by shaking in 250 ml baffled flasks, grown at 30° C. and sampled periodically for measurements of turbidity and Bap activity as described in Wanner, B. L. and R. McSharry, Phosphate-controlled Gene Expression in *Escherichia coli* using Mudl-directed lacZ Fusions, *J. Mol. Biol.* Vol. 158, pp. 347–363 (1982). FIG. 1 shows results thus obtained using *E. coli* K-12 phn(EcoB) BW15268. This strain was obtained by P1 phage transduction of the *E. coli* phn(EcoB) genes into *E. coli* K-12. In particular, FIG. 1A provides a plot of O.D. at 420 over time, and Figure 1B provides a differential plot of Bap synthesis in the *E. coli* cultures. FIG. 2 shows results using *Ent. aerogenes* BW16627 in the same media. This strain was obtained by selection of a spontaneous streptomycin resistant mutant of *Ent. aerogenes* IFO 12010 (ATCC 15038). In particular FIG. 2A provides a plot of O.D. at 420 over time, and FIG. 2B provides a differential plot of Bap synthesis in the *Ent aerogenes* cultures. The scale in FIG. 2B was expanded to show enzyme derepression in the AEPn culture; lines are continuous with data points off the scale.

As shown, growth of each of the bacteria on the phosphonates and phosphite was nearly as good as on high Pi and substantially greater than growth on low Pi. Similarly, Bap production was dramatically higher when the phosphonates or phosphite were used. These results highlight the significance of the invention and evidence the outstanding increases in production efficiency of PSI gene products which are achievable by culturing a bacterium with C-P lyase activity using phosphonates and phosphites as the predominant phosphorus source for growth. As an additional advantage, use of phosphonates and phosphites as the predominant phosphorus source prevents accumulation of mutants unable to express phosphate-regulated genes by demanding expression of genes for the C-P lyase pathway during growth.

All publications cited herein are hereby incorporated by reference in their entirety.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A method for enhanced production and recovery of phosphate starvation inducible gene product, comprising:
   culturing an *Escherichia coli* or *Enterobacter aerogenes* bacterium having C-P lyase activity on an organic phosphonate, a phosphite, or a mixture thereof as the predominant phosphorus source for growth to result in enhanced production of the gene product; and recovering and purifying the gene product.

2. The method of claim 1 wherein the bacterium is cultured on phosphonate as the predominant phosphorus source for growth.

3. The method of claim 1 wherein the bacterium is cultured on phosphite as the predominant phosphorus source for growth.

4. The method of claim 1 wherein the phosphonate or phosphite or mixture is present in molar excess to any inorganic phosphate present.

5. The method of claim 1 wherein the gene product is produced at an enhanced rate throughout the logarithmic growth phase of the bacterium.

6. The method of claim 1 wherein the phosphonate or phosphite or mixture thereof is included in sufficient amount so as not to limit the growth yield of the bacterium.

7. The method of claim 6 wherein the gene product is produced at an enhanced rate throughout the logarithmic growth phase of the bacterium.

8. The method of claim 7 wherein the bacterium is cultured on phosphonate as the predominant phosphorus source for growth.

9. The method of claim 1 wherein the bacterium is *Enterobacter aerogenes*.

10. The method of claim 1 wherein the bacterium is *Escherichia coli*.

11. The method of claim 1 wherein the phosphonate is an unsubstituted alkylphosphonate.

12. The method of claim 10 wherein the phosphonate is a substituted or unsubstituted alkylphosphonate.

13. The method of claim 11 wherein the phosphonate is selected from the group consisting of methylphosphonate and ethylphosphonate.

14. The method of claim 12 wherein the phosphonate is selected from the group consisting of methylphosphonate, ethylphosphonate, α-aminoethylphosphonate, or phosphonoacetate.

15. The method of claim 14 wherein the phosphonate is methylphosphonate or ethylphosphonate.

16. A method for preparing a phosphate starvation inducible gene product, comprising:
   culturing an *Escherichia coli* or *Enterobacter aerogenes* bacterium having C-P lyase activity in a fermentation medium wherein the predominant phosphorus source for growth is a phosphite, an organic phosphonate, or a mixture thereof, to accumulate said gene product;
   releasing said gene product from the bacterium; and recovering and purifying said gene product.

17. The method of claim 16 wherein said releasing includes breaking bacterial cells.

18. The method of claim 16 wherein the predominant phosphorus source for growth is phosphonate.

19. The method of claim 10 including the step of purifying said gene product to substantially pure form.

* * * * *

UNITED STATES PATENT AND TRADEMARK OFFICE
CERTIFICATE OF CORRECTION

PATENT NO. : 5,413,920
DATED : May 9, 1995
INVENTOR(S) : Barry L. Wanner, Ki-Sung Lee and William W. Metcalf It is certified that error appears in the above-identified patent and that said Letters Patent is hereby corrected as shown below:

In column 4, line 65, please delete "phosphonae" and insert in lieu thereof --phosphonate--.

Signed and Sealed this

Eighteenth Day of July, 1995

Attest:

BRUCE LEHMAN

Attesting Officer

Commissioner of Patents and Trademarks